United States Patent
Paquet et al.

(10) Patent No.: US 9,055,925 B2
(45) Date of Patent: Jun. 16, 2015

(54) SYSTEM AND METHOD FOR REDUCING FALSE ALARMS ASSOCIATED WITH VITAL-SIGNS MONITORING

(75) Inventors: Pierre Paquet, Quebec (CA); Stephen Lewis, San Diego, CA (US)

(73) Assignee: CAREFUSION 303, INC., San Diego, CA (US)

(*) Notice: Subject to any disclaimer, the term of this patent is extended or adjusted under 35 U.S.C. 154(b) by 0 days.

(21) Appl. No.: 12/844,794

(22) Filed: Jul. 27, 2010

(65) Prior Publication Data

US 2012/0029314 A1 Feb. 2, 2012

(51) Int. Cl.
*A61B 5/00* (2006.01)
*G08B 21/02* (2006.01)
*G08B 21/00* (2006.01)
*G06F 19/00* (2011.01)
*G08B 25/00* (2006.01)

(52) U.S. Cl.
CPC ............. *A61B 5/6833* (2013.01); *G08B 25/006* (2013.01); *G08B 21/0211* (2013.01); *G06F 19/3418* (2013.01); *A61B 5/72* (2013.01); *A61B 5/0008* (2013.01); *A61B 5/746* (2013.01); *A61B 5/002* (2013.01); *A61B 2560/0412* (2013.01)

(58) Field of Classification Search
CPC ............. A61B 5/0002; G08B 21/0211; G06F 19/30–19/366
USPC ......... 600/300–301, 306–309, 316, 323, 324, 600/339, 341, 344, 333, 357, 363–365, 600/372–374, 377–379, 382–384, 386–394, 600/481, 485, 500–503, 508, 515–519, 600/529–531, 544–547, 549, 587–595; 705/2–3; 128/920–925

See application file for complete search history.

(56) References Cited

U.S. PATENT DOCUMENTS

| 3,677,261 A | 7/1972 | Day |
| 3,830,224 A | 8/1974 | Vanzetti et al. |
| 4,121,574 A | 10/1978 | Lester |
| 4,396,020 A | 8/1983 | Wolff et al. |
| 4,530,366 A | 7/1985 | Nessi et al. |

(Continued)

FOREIGN PATENT DOCUMENTS

| EP | 1748289 A2 | 1/2007 |
| JP | 61003019 | 1/1986 |

(Continued)

OTHER PUBLICATIONS

Akyldiz, I.F. et al.; "Wireless Multimedia Sensor Networks: A survey." IEEE Wireless Communications. Dec. 2007, pp. 32-39.

(Continued)

*Primary Examiner* — William Thomson
*Assistant Examiner* — Marie Archer
(74) *Attorney, Agent, or Firm* — McDermott Will & Emery LLP

(57) ABSTRACT

Systems and methods of reducing false alarms associated with a vital-sign monitor are disclosed. One or more data samples of a vital sign of a patient are generated at a first sampling rate in a normal mode of operation. Whether the one or more data samples satisfy an alert condition is determined. An alert mode of operation is entered into if the alert condition is satisfied. One or more additional data samples of the vital sign are generated at a second sampling rate higher than the first sampling rate in the alert mode.

19 Claims, 10 Drawing Sheets

(56) References Cited

U.S. PATENT DOCUMENTS

| | | | |
|---|---|---|---|
| 4,686,998 A | 8/1987 | Robbins | |
| 4,708,146 A | 11/1987 | Lane | |
| 4,765,340 A | 8/1988 | Sakai et al. | |
| 4,838,273 A | 6/1989 | Cartmell | |
| 4,967,765 A | 11/1990 | Turner et al. | |
| 5,050,612 A | 9/1991 | Matsumura | |
| 5,153,584 A * | 10/1992 | Engira | 340/870.18 |
| 5,258,577 A | 11/1993 | Clements | |
| 5,273,036 A | 12/1993 | Kronberg et al. | |
| 5,344,335 A | 9/1994 | Scholz et al. | |
| 5,353,793 A | 10/1994 | Bornn | |
| 5,401,100 A | 3/1995 | Thackston et al. | |
| 5,511,553 A | 4/1996 | Segalowitz | |
| 5,544,661 A * | 8/1996 | Davis et al. | 600/513 |
| 6,030,342 A | 2/2000 | Amano et al. | |
| 6,042,966 A | 3/2000 | Cheu | |
| 6,222,456 B1 * | 4/2001 | Tice | 340/630 |
| 6,287,252 B1 * | 9/2001 | Lugo | 600/300 |
| 6,324,426 B1 | 11/2001 | Thompson | |
| 6,454,708 B1 | 9/2002 | Ferguson et al. | |
| 6,468,261 B1 | 10/2002 | Small et al. | |
| 6,494,829 B1 | 12/2002 | New, Jr. et al. | |
| 6,517,497 B2 | 2/2003 | Rymut et al. | |
| 6,636,754 B1 | 10/2003 | Baura et al. | |
| 6,740,059 B2 | 5/2004 | Flaherty | |
| 6,950,688 B2 | 9/2005 | Axelgaard et al. | |
| 6,963,772 B2 | 11/2005 | Bloom et al. | |
| 6,980,112 B2 | 12/2005 | Nee | |
| 7,052,472 B1 | 5/2006 | Miller et al. | |
| 7,061,858 B1 | 6/2006 | Di Benedetto et al. | |
| 7,198,600 B2 | 4/2007 | Tamaki et al. | |
| 7,355,512 B1 * | 4/2008 | Al-Ali | 340/511 |
| RE40,470 E | 8/2008 | Fitzpatrick et al. | |
| 7,434,991 B2 | 10/2008 | Harr et al. | |
| 7,447,526 B2 | 11/2008 | Kim et al. | |
| 7,542,437 B1 | 6/2009 | Redi et al. | |
| 7,639,652 B1 | 12/2009 | Amis et al. | |
| 7,645,263 B2 | 1/2010 | Angel et al. | |
| 7,668,588 B2 | 2/2010 | Kovacs | |
| 7,924,150 B2 * | 4/2011 | Baldus et al. | 340/539.12 |
| 7,959,574 B2 * | 6/2011 | Bardy | 600/484 |
| 7,962,188 B2 * | 6/2011 | Kiani et al. | 600/310 |
| 8,007,436 B2 | 8/2011 | Katayama | |
| 8,200,320 B2 | 6/2012 | Kovacs | |
| 8,228,188 B2 | 7/2012 | Key et al. | |
| 8,506,480 B2 | 8/2013 | Banet et al. | |
| 8,721,562 B2 | 5/2014 | Abreu | |
| 2001/0047127 A1 | 11/2001 | New, Jr. et al. | |
| 2002/0007676 A1 | 1/2002 | Ward et al. | |
| 2002/0013538 A1 | 1/2002 | Teller | |
| 2002/0045836 A1 | 4/2002 | Alkawwas | |
| 2002/0099277 A1 | 7/2002 | Harry et al. | |
| 2002/0107436 A1 | 8/2002 | Barton et al. | |
| 2003/0004403 A1 | 1/2003 | Drinan et al. | |
| 2003/0040305 A1 | 2/2003 | Ng et al. | |
| 2003/0069510 A1 | 4/2003 | Semler et al. | |
| 2003/0191445 A1 | 10/2003 | Wallen et al. | |
| 2003/0212319 A1 | 11/2003 | Magill | |
| 2003/0229809 A1 | 12/2003 | Wexler et al. | |
| 2004/0015058 A1 | 1/2004 | Besson et al. | |
| 2004/0030259 A1 | 2/2004 | Dae et al. | |
| 2004/0062133 A1 | 4/2004 | Tsuji | |
| 2004/0116822 A1 | 6/2004 | Lindsey | |
| 2004/0215098 A1 | 10/2004 | Barton et al. | |
| 2004/0236188 A1 * | 11/2004 | Hutchinson et al. | 600/300 |
| 2005/0085706 A1 | 4/2005 | Perrault et al. | |
| 2005/0101843 A1 | 5/2005 | Quinn et al. | |
| 2005/0131288 A1 | 6/2005 | Turner et al. | |
| 2005/0159653 A1 | 7/2005 | Lijima et al. | |
| 2005/0195079 A1 * | 9/2005 | Cohen | 340/539.12 |
| 2005/0228297 A1 | 10/2005 | Banet et al. | |
| 2005/0228299 A1 | 10/2005 | Banet | |
| 2005/0231350 A1 * | 10/2005 | Littrell et al. | 340/511 |
| 2005/0245831 A1 | 11/2005 | Banet | |
| 2005/0245839 A1 | 11/2005 | Stivoric et al. | |
| 2005/0249263 A1 | 11/2005 | Yerlikaya et al. | |
| 2005/0251128 A1 | 11/2005 | Amoah | |
| 2006/0009697 A1 | 1/2006 | Banet et al. | |
| 2006/0047987 A1 | 3/2006 | Prabhakaran et al. | |
| 2006/0094971 A1 | 5/2006 | Drew | |
| 2006/0098576 A1 | 5/2006 | Brownrigg et al. | |
| 2006/0155183 A1 | 7/2006 | Kroecker et al. | |
| 2006/0202816 A1 | 9/2006 | Crump et al. | |
| 2006/0224349 A1 | 10/2006 | Butterfield | |
| 2006/0276714 A1 | 12/2006 | Holt et al. | |
| 2007/0032706 A1 | 2/2007 | Kamath et al. | |
| 2007/0041424 A1 | 2/2007 | Lev et al. | |
| 2007/0099678 A1 | 5/2007 | Kim et al. | |
| 2007/0123756 A1 | 5/2007 | Kitajima et al. | |
| 2007/0129622 A1 | 6/2007 | Bourget et al. | |
| 2007/0135866 A1 | 6/2007 | Baker et al. | |
| 2007/0142715 A1 | 6/2007 | Banet et al. | |
| 2007/0191728 A1 | 8/2007 | Shennib | |
| 2007/0208233 A1 | 9/2007 | Kovacs | |
| 2007/0219434 A1 | 9/2007 | Abreu | |
| 2007/0293781 A1 | 12/2007 | Sims et al. | |
| 2008/0042866 A1 | 2/2008 | Morse et al. | |
| 2008/0091090 A1 | 4/2008 | Guillory et al. | |
| 2008/0097178 A1 | 4/2008 | Banet et al. | |
| 2008/0114220 A1 | 5/2008 | Banet et al. | |
| 2008/0119707 A1 | 5/2008 | Stafford | |
| 2008/0143512 A1 | 6/2008 | Wakisaka et al. | |
| 2008/0183054 A1 * | 7/2008 | Kroeger et al. | 600/301 |
| 2008/0200770 A1 | 8/2008 | Hubinette | |
| 2008/0200774 A1 | 8/2008 | Luo | |
| 2008/0208026 A1 * | 8/2008 | Noujaim et al. | 600/365 |
| 2008/0221399 A1 | 9/2008 | Zhou et al. | |
| 2008/0275327 A1 | 11/2008 | Faarbaek et al. | |
| 2008/0294065 A1 | 11/2008 | Waldhoff et al. | |
| 2008/0305154 A1 | 12/2008 | Yanaki | |
| 2009/0018409 A1 | 1/2009 | Banet et al. | |
| 2009/0054737 A1 | 2/2009 | Magar et al. | |
| 2009/0062670 A1 | 3/2009 | Sterling et al. | |
| 2009/0069642 A1 * | 3/2009 | Gao et al. | 600/300 |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076345 A1 | 3/2009 | Manicka et al. | |
| 2009/0076346 A1 | 3/2009 | James et al. | |
| 2009/0076350 A1 * | 3/2009 | Bly et al. | 600/301 |
| 2009/0076363 A1 | 3/2009 | Bly et al. | |
| 2009/0076364 A1 | 3/2009 | Libbus et al. | |
| 2009/0076405 A1 | 3/2009 | Amurthur et al. | |
| 2009/0105549 A1 | 4/2009 | Smith et al. | |
| 2009/0105605 A1 | 4/2009 | Abreu | |
| 2009/0131759 A1 | 5/2009 | Sims et al. | |
| 2009/0131754 A1 * | 5/2009 | Sweitzer et al. | 600/323 |
| 2009/0182204 A1 | 7/2009 | Semler et al. | |
| 2009/0203974 A1 | 8/2009 | Hickle | |
| 2009/0227877 A1 | 9/2009 | Tran | |
| 2009/0259139 A1 | 10/2009 | Stapien et al. | |
| 2009/0270744 A1 | 10/2009 | Prstojevich et al. | |
| 2009/0271681 A1 | 10/2009 | Piret et al. | |
| 2010/0036212 A1 | 2/2010 | Rieth | |
| 2010/0056886 A1 * | 3/2010 | Hurtubise et al. | 600/324 |
| 2010/0081949 A1 | 4/2010 | Derby, Jr. | |
| 2010/0113894 A1 | 5/2010 | Padiy | |
| 2010/0222688 A1 * | 9/2010 | Fischell et al. | 600/509 |
| 2010/0298656 A1 * | 11/2010 | McCombie et al. | 600/301 |
| 2010/0298895 A1 | 11/2010 | Ghaffari et al. | |
| 2010/0323634 A1 | 12/2010 | Kimura | |
| 2011/0004076 A1 | 1/2011 | Janna et al. | |
| 2011/0060252 A1 | 3/2011 | Simonsen et al. | |
| 2011/0066062 A1 | 3/2011 | Banet et al. | |
| 2011/0144470 A1 * | 6/2011 | Mazar et al. | 600/391 |
| 2011/0160601 A1 | 6/2011 | Wang et al. | |
| 2011/0176465 A1 | 7/2011 | Panta et al. | |
| 2011/0182213 A1 | 7/2011 | Forssell et al. | |
| 2011/0224557 A1 | 9/2011 | Banet et al. | |
| 2012/0029300 A1 | 2/2012 | Paquet | |
| 2012/0029308 A1 | 2/2012 | Paquet | |
| 2012/0029314 A1 | 2/2012 | Paquet et al. | |
| 2012/0108920 A1 | 5/2012 | Bly et al. | |

(56) References Cited

U.S. PATENT DOCUMENTS

FOREIGN PATENT DOCUMENTS

| | | |
|---|---|---|
| JP | 2002-507131 | 3/2002 |
| JP | 2004-503266 | 2/2004 |
| JP | 2005-521453 | 7/2005 |
| JP | 2009-544065 | 12/2009 |
| KR | 20070097725 | 10/2007 |
| KR | 100949150 | 3/2010 |
| WO | WO90/12606 | 11/1990 |

OTHER PUBLICATIONS

Arisha, K. et al. "System-Level Power Optimization for wireless Multimedia Communication." Editors: Ramesh K. and Goodman, D.; Springer US; 2002, pp. 21-40.

Cardei, M. et al.; "Improving Wireless Sensor Network Lifetime through Power Aware Organization"; Wireless Networks 11, 222-240. 2005.

Davidson, K. G. et al., "Measurement of tidal volume by using transthoracic impedance variations in rats," J. Appl. Physiol. 86:759-766, 1999.

Ernst. J.M. et al, "Impedance Penumography: noise as signal in impedance cardiography," Psychophysiology, 36 (1999) 333-338.

Freundlich J.J. et al., Electrical Impedance Pneumography for Simple Nonrestritive Continuous Monitoring of Respiratory Rate, Rhythm and Tidal Volume for Surgical Patients, Chest, 65, pp. 181-184, 1974.

Herman, T. et al.; "A Distributed TDMA Slot Assignment Algorithm for Wireless Sensor Networks"; S. Nikoletseas and J. Rolim (Eds.): Algosensors 2004, LNCS 3121, pp. 45-58, 2004, Springer-Verlag Berlin Heidelberg 2004.

Hohlt, B. et al. "Flexible Power Scheduling for Sensor Networks," IPSN'04, Apr. 26-27, 2004, Berkeley, California, USA. p. 1-10.

Kelkar, S. P. et al., "Development of Movement artifact free breathing monitor," J. Instrum. Soc. India 38(1) 34-43, 2008.

Lee, W. L.; "Flexible-Schedule-Based TDMA Protocol for Fault-Tolerant and Energy-Efficient Wireless Sensor Networks," IEEE Transactions on Parallel and Distributed Systems, vol. 19, No. 6, Jun. 2008; pp. 851-864.

Lee, W. L.; "Flexible-Schedule-Based TDMA Protocols for Supporting Fault-Tolerance, On-Demand TDMA Slot Transfer, and Peer-to-Peer Communication in Wireless Sensor Networks;" Thesis for the degree of Doctor in Philosophy, University of Western Australia, 2007, pp. 1-213.

Loriga, G., et al., "Textile sensing interfaces for cardiopulmonary signs monitoring," Proceedings of the 2005 IEEE Engineering in Medicine and Biology 27th Annual Conference Shanghai, China, Sep. 1-4, 2005, pp. 7349-7352.

Luo, S. et al., "The electrode system in Impedance-Based Ventilation Measurement," IEEE Transactions of biomedical Engineering, vol. 39, No. 11, Nov. 1992, pp. 1130-1140.

Matthews, R., et al., "A Wearable Physiological Sensor Suite for Unobtrusive Monitoring of Physiological and Cognitive State," Proceedings of the 29th Annual International Conference of the IEEE EMBS Cite Internationale, Lyon, France, Aug. 23-26, 2007, pp. 1-6.

Pacela, A.F. "Impedance Pneumograph, a survey of instrumentation techniques," Med. & Biol. Engineering, vol. 4, pp. 1-5, 1966.

Pantazis, N.A. et al.; "Energy efficiency in wireless sensor networks using sleep mode TDMA scheduling," Ad Hoc Networks 7 (2009) 322-343.

Paradiso, R. et al., "A wearable health care system based on knitted integrated sensors," IEEE transactions on Information Technology in biomedicine, vol. 9, No. 3, Sep. 2005, pp. 337-344.

Park, et al., "Development of Flexible Self Adhesive Patch for Professional Heat Stress Monitoring Service," Proceedings of the 2005 IEEE Engineering in Medicine and Biology 27th Annual Conference Shanghai, China, Sep. 1-4, 2005, pp. 3789-3792.

Rashid, R. A. et al; "Development of Energy Aware TDMA-Based MAC Protocol for Wireless Sensor Network System," European Journal of Scientific, vol. 30 No. 4 (2009), pp. 571-578.

Shaw, G.A. et al., "Warfighter Physiological and Environmental Monitoring: A Study for the U.S. Army Research Institute in Environmental Medicine and the Soldier Systems Center," 2004, Lincoln Laboratory, MIT, pp. 1-141.

Zheng, W. W. et al. "Adaptive-frame-based Dynamic Slot Assignment Protocol for Tactical Data Link System," 2009 International Conference of Networks Security, Wireless Communications and Trusted Computing, IEEE, pp. 709-714.

Final Office Action, dated Oct. 28, 2012 for U.S. Appl. No. 12/844,771.

Brown, B.H. et al., "Bipolar and Tetrapolar transfer impedance measurements from volume conductor," Electronics Letters, vol. 35, No. 25, 2000, pp. 2060-2062.

Cooley, W.L. et al., "A new design for an impedance pneumograph," Journal of Applied Physiology, vol. 25, No. 4, 1968, pp. 429-432.

Grenvik, A. et al., "Impedance Pneumography," Chest, vol. 62, No. 4, Oct. 1972, pp. 439- 443.

Holt, T. et al., "Monitoring and recording of physiological data of the manned space flight program," Supplement to IEEE Transactions on Aerospace, Jun. 1965, pp. 341-344.

Miller, Matthew J., et al., "On-Demand TDMA Scheduling for Energy Conservation in Sensor Networks," Technical Report, Jun. 2004. p. 1-10.

Murat, B., "Electrical Impedence Plethysmography," Wiley Encyclopedia of Biomedical Engineering, 2006, pp. 1-10.

NPL_VitalSense_2006, pp. 1-2.

Poon, C. S. et al., "Evaluation of two noninvasive techniques for exercise ventilatory measurements," IEEE Engineering in Medicine and Biology conference, 1988, pp. 0823-0824.

Shakian, A. V. et al., "Electrode Motion Artifacts in Electrical Impedence Pneumography," IEEE Transactions in Biomedical Engineering, vol. BME-32, No. 6, Jun. 1985, pp. 448-451.

Office Actions issued in U.S. Appl. No. 12/844,801 dated Aug. 14, 2014, and U.S. Appl. No. 12/844,794, dated Sep. 26, 2014.

* cited by examiner

SYSTEM AND METHOD FOR REDUCING FALSE ALARMS ASSOCIATED WITH VITAL-SIGNS MONITORING

CROSS-REFERENCES TO RELATED APPLICATIONS

The following applications disclose certain common subject matter with the present application: A Vital-Signs Monitor with Encapsulation Arrangement, Ser. No. 12/844,766; A Vital-Signs Monitor with Spaced Electrodes, Ser. No. 12/844,769; A Vital-Signs Patch Having a Strain Relief, Ser. No. 12/844,774; A Temperature Probe Suitable for Axillary Reading, Ser. No. 12/844,775; System and Method for Monitoring Body Temperature of a Person, Ser. No. 12/844,771; A System and Method for Storing and Forwarding Data from a Vital-Signs Monitor, Ser. No. 12/844,780; System and Method for Saving Battery Power in a Vital Signs Monitor, 12/844,789; A System and Method for Conserving Battery Power in a Patient Monitoring System, Ser. No. 12/844,796; A System and Method for Saving Battery Power in a Patient Monitoring System, Ser. No. 12/844,801; A System And Method for Tracking Vital-Signs Monitor Patches, Ser. No. 12/844,788; A System And Method for Location Tracking of Patients in a Vital-Signs Monitoring System, Ser. No. 12/844,781; A System And Method for Reducing False Alarms Based on Motion and Location Sensing, Ser. No. 12/844,765; all of the listed applications filed on Jul. 27, 2010.

FIELD

The present disclosure generally relates to systems and methods of physiological monitoring, and, in particular, relates to systems and methods for reducing false alarms associated with a vital-sign monitor.

DESCRIPTION OF THE RELATED ART

Some of the most basic indicators of a person's health are those physiological measurements that reflect basic body functions and are commonly referred to as a person's "vital signs." The four measurements commonly considered to be vital signs are body temperature, pulse rate, blood pressure, and respiratory rate. Most or all of these measurements are performed routinely upon a patient when they arrive at a healthcare facility, whether it is a routine visit to their doctor or arrival at an Emergency Room (ER).

Vital signs are frequently taken by a nurse using basic tools including a thermometer to measure body temperature, a sphygmomanometer to measure blood pressure, and a watch to count the number of breaths or the number of heart beats in a defined period of time, typically 10 seconds, which is then converted to a "per minute" rate. If a patient's pulse is weak, it may not be possible to detect a pulse by hand and the nurse may use a stethoscope to amplify the sound of the patient's heart beat so that she can count the beats.

When a patient is admitted to a hospital, it is common for vital signs to be measured and recorded at regular intervals during the patient's stay to monitor their condition. A typical interval is 4 hours, which leads to the undesirable requirement for a nurse to awaken a patient in the middle of the night to take vital sign measurements.

When a patient is admitted to an ER, it is common for a nurse to do a "triage" assessment of the patient's condition that will determine how quickly the patient receives treatment. During busy times in an ER, a patient who does not appear to have a life-threatening injury may wait for hours until more-serious cases have been treated. While the patient may be reassessed at intervals while awaiting treatment, the patient may not be under observation between these reassessments.

Measuring certain vital signs is normally intrusive at best and difficult to do on a continuous basis. Measurement of body temperature, for example, is commonly done by placing an oral thermometer under the tongue or placing an infrared thermometer in the ear canal such that the tympanic membrane, which shared blood circulation with the brain, is in the sensor's field of view. Other countries report temperatures made by placing a thermometer under the arm, referred to as an "axillary" measurement as axilla is the Latin word for armpit. Skin temperature can be measured using a stick-on strip that may contain panels that change color to indicate the temperature of the skin below the strip.

Measurement of respiration is easy for a nurse to do, but relatively complicated for equipment to achieve. A method of automatically measuring respiration is to encircle the upper torso with a flexible band that can detect the physical expansion of the rib cage when a patient inhales. An alternate technique is to measure a high-frequency electrical impedance between two electrodes placed on the torso and detect the change in impedance created when the lungs fill with air. The electrodes are typically placed on opposite sides of one or both lungs, resulting in placement on the front and back or on the left and right sides of the torso, commonly done with adhesive electrodes connected by wires or by using a torso band with multiple electrodes in the strap.

Measurement of pulse is also relatively easy for a nurse to do and intrusive for equipment to achieve. A common automatic method of measuring a pulse is to use an electrocardiograph (ECG or EKG) to detect the electrical activity of the heart. An EKG machine may use up to 10 electrodes placed at defined points on the body to detect various signals associated with the heart function. Another common piece of equipment is simply called a "heart rate monitor." Widely sold for use in exercise and training, heart rate monitors commonly consist of a torso band, in which are embedded two electrodes held against the skin and a small electronics package. Such heart rate monitors can communicate wirelessly to other equipment such as a small device that is worn like a wrist watch and that can transfer data wirelessly to a PC.

Nurses are expected to provide complete care to an assigned number of patients. The workload of a typical nurse is increasing, driven by a combination of a continuing shortage of nurses, an increase in the number of formal procedures that must be followed, and an expectation of increased documentation. Replacing the manual measurement and logging of vital signs with a system that measures and records vital signs would enable a nurse to spend more time on other activities and avoid the potential for error that is inherent in any manual procedure.

SUMMARY

For some or all of the reasons listed above, there is a need for a hospital to be able to continuously monitor its patients in different settings within the hospital. In addition, it is desirable for this monitoring to be done with limited interference with a patient's mobility or interfering with their other activities.

Embodiments of the patient monitoring system disclosed herein measure certain vital-sign readings of a patient, which include respiratory rate, pulse rate, and body temperature, on a regular basis and compare these measurements to preset limits.

In addition, certain embodiments of the patient monitoring system disclosed herein can send alarm notifications to a hospital system if the vital-sign readings satisfy an alarm condition. It is desirable to reduce or eliminate false positives in the alarm notifications so as to avoid unnecessary trips or other actions of a healthcare provider that such false positives can cause.

In one aspect of the present disclosure, a method of reducing false alarms associated with a vital-sign monitor is disclosed. The method can comprise generating one or more data samples of a vital sign of a patient at a first sampling rate in a normal mode of operation. The method can further comprise determining whether the one or more data samples satisfies an alert condition. The method can further comprise entering an alert mode of operation if the alert condition is satisfied. The method can further comprise generating one or more additional data samples of the vital sign at a second sampling rate higher than the first sampling rate in the alert mode.

In one aspect of the present disclosure, a vital sign monitoring system is disclosed. The system can comprise a vital-sign monitor configured to monitor one or more vital signs of a patient. The system can further comprise a surveillance server configured to gather data relating to the one or more vital signs of the patient from the vital-sign monitor. The vital-sign monitor can be further configured to generate one or more data samples of a vital sign of a patient at a first sampling rate in a normal mode of operation, determine whether the one or more data samples satisfy an alert condition, enter an alert mode if the alarm condition is satisfied, and generate one or more additional data samples of the vital sign at a second sampling rate higher than the first sampling rate in the alert mode.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Continuous monitoring of patients in a hospital is desirable at least to ensure that patients do not suffer an un-noticed sudden deterioration in their condition or a secondary injury during their stay in the hospital. It is impractical to provide continuous monitoring by a clinician and cumbersome to connect sensors to a patient, which are then connected to a fixed monitoring instrument by wires. Furthermore, systems that sound an alarm when the measured value exceeds a threshold value may sound alarms so often and in situations that are not truly serious that such alarms are ignored by clinicians.

Measuring vital signs is difficult to do on a continuous basis. Accurate measurement of cardiac pulse, for example, can be done using an electrocardiograph (ECG or EKG) to detect the electrical activity of the heart. An EKG machine may use up to 10 electrodes placed at various points on the body to detect various signals associated with the heart function. Another common piece of equipment is termed a "heart rate monitor." Widely sold for use in exercise and physical training, heart rate monitors may consist of a torso band in which are embedded two electrodes held against the skin and a small electronics package. Such heart rate monitors can communicate wirelessly to other equipment such as a small device that is worn like a wrist watch that can transfer data wirelessly to a personal computer (PC).

Certain exemplary embodiments of the present disclosure include a system that comprises a vital-signs monitor patch that is attached to the patient, and a bridge that communicates with monitor patches and links them to a central server that processes the data, where the server also sends data and alarms to the hospital system according to algorithms and protocols defined by the hospital.

The construction of the vital-signs monitor patch is described according to certain aspects of the present disclosure. As the patch may be worn continuously for a period of time that may be several days, as is described in the following disclosure, it is desirable to encapsulate the components of the patch such that the patient can bathe or shower and engage in their normal activities without degradation of the patch function. An exemplary configuration of the construction of the patch to provide a hermetically sealed enclosure about the electronics is disclosed.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1:
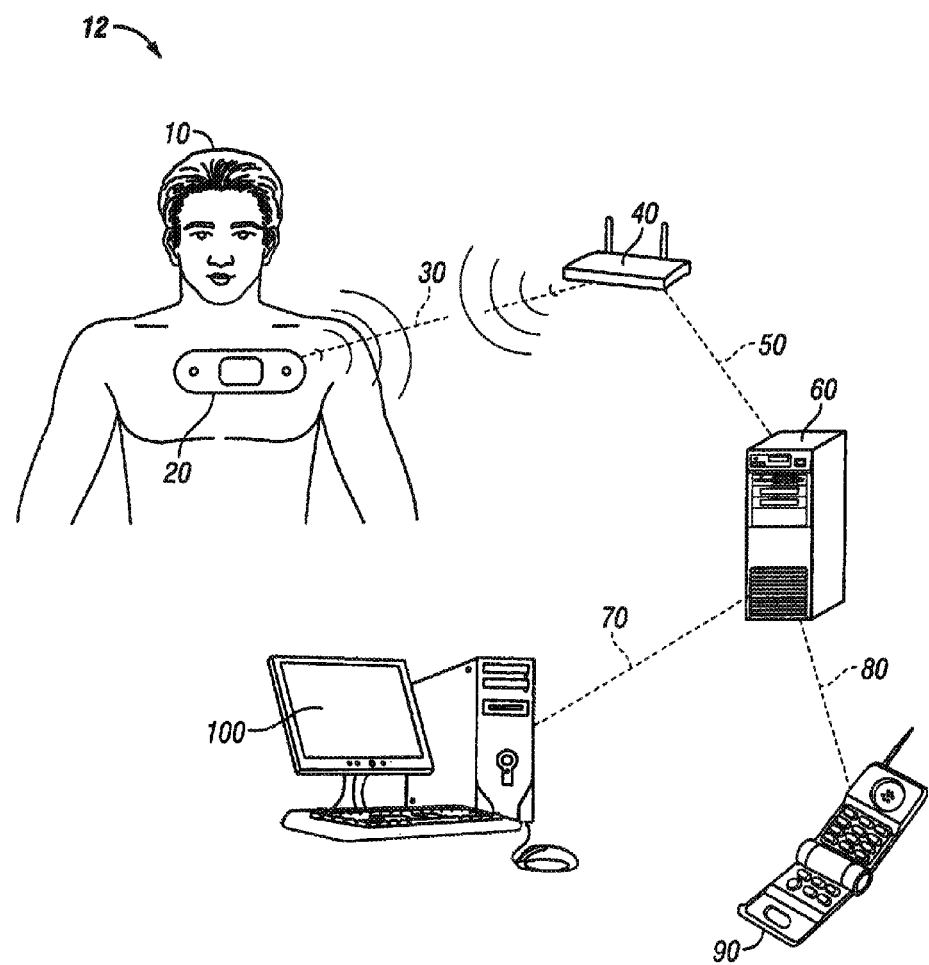
FIG. 1 is a diagram illustrating an exemplary embodiment of a patient monitoring system according to certain aspects of the present disclosure.

FIG. 1 discloses a vital sign monitoring system according to certain embodiments of the present disclosure. The vital sign monitoring system 12 includes vital-signs monitor patch 20, bridge 40, and surveillance server 60 that can send messages or interact with peripheral devices exemplified by mobile device 90 and workstation 100.

Monitor patch 20 resembles a large adhesive bandage and is applied to a patient 10 when in use. It is preferable to apply the monitor patch 20 to the upper chest of the patient 10 although other locations may be appropriate in some circumstances. Monitor patch 20 incorporates one or more electrodes (not shown) that are in contact with the skin of patient 10 to measure vital signs such as cardiac pulse rate and respiration rate. Monitor patch 20 also may include other sensors such as an accelerometer or a temperature sensor to measure other characteristics associated with the patient. Monitor patch 20 also includes a wireless transmitter that can both transmit and receive signals. This transmitter is preferably a short-range, low-power radio frequency (RF) device operating in one of the industrial, scientific and medical (ISM) radio bands. One ISM band in the United States (US) is, for example, centered at 915 MHz. An example of an equivalent band in the European Union (EU) is centered at 868 MHz. Other frequencies of operation may be possible dependent upon local regulations and interference from other wireless devices.

Surveillance server 60 may be a standard computer server connected to the hospital communication network and preferably located in the hospital data center or computer room, although other locations may be employed. The server 60 stores and processes signals related to the operation of the patient monitoring system 12 disclosed herein including the association of individual monitor patches 20 with patients 10 and measurement signals received from multiple monitor patches 20. Hence, although only a single patient 10 and monitor patch 20 are depicted in FIG. 1, the server 60 is able to monitor the monitor patches 20 for multiple patients 10.

Bridge 40 is a device that connects, or "bridges", between monitor patch 20 and server 60. Bridge 40 communicates with monitor patch 20 over communication link 30 operating, in these exemplary embodiments, at approximately 915 MHz and at a power level that enables communication link 30 to function up to a distance of approximately 3 meters. It is preferable to place a bridge 40 in each room and at regular intervals along hallways of the healthcare facility where it is desired to provide the ability to communicate with monitor patches 20. Bridge 40 also is able to communicate with server 60 over network link 50 using any of a variety of computer communication systems including hardwired and wireless Ethernet using protocols such as 802.11a/b/g or 802.3af. As the communication protocols of communication link 30 and network link 50 may be very different, bridge 40 provides data buffering and protocol conversion to enable bidirectional signal transmission between monitor patch 20 and server 60.

While the embodiments illustrated by FIG. 1 employ a bridge 20 to provide communication link between the monitor patch 20 and the server 60, in certain alternative embodiments, the monitor patch 20 may engage in direct wireless communication with the server 60. In such alternative embodiments, the server 60 itself or a wireless modem connected to the server 60 may include a wireless communication system to receive data from the monitor patch 20.

In use, a monitor patch 20 is applied to a patient 10 by a clinician when it is desirable to continuously monitor basic vital signs of patient 10 while patient 10 is, in this embodiment, in a hospital. Monitor patch 20 is intended to remain attached to patient 10 for an extended period of time, for example, up to 5 days in certain embodiments, limited by the battery life of monitor patch 20. In some embodiments, monitor patch 20 is disposable when removed from patient 10.

Server 60 executes analytical protocols on the measurement data that it receives from monitor patch 20 and provides this information to clinicians through external workstations 100, preferably personal computers (PCs), over the hospital network 70. Server 60 may also send messages to mobile devices 90, such as cell phones or pagers, over a mobile device link 80 if a measurement signal exceeds specified parameters. Mobile device link 80 may include the hospital network 70 and internal or external wireless communication systems that are capable of sending messages that can be received by mobile devices 90.

Figure 2A:
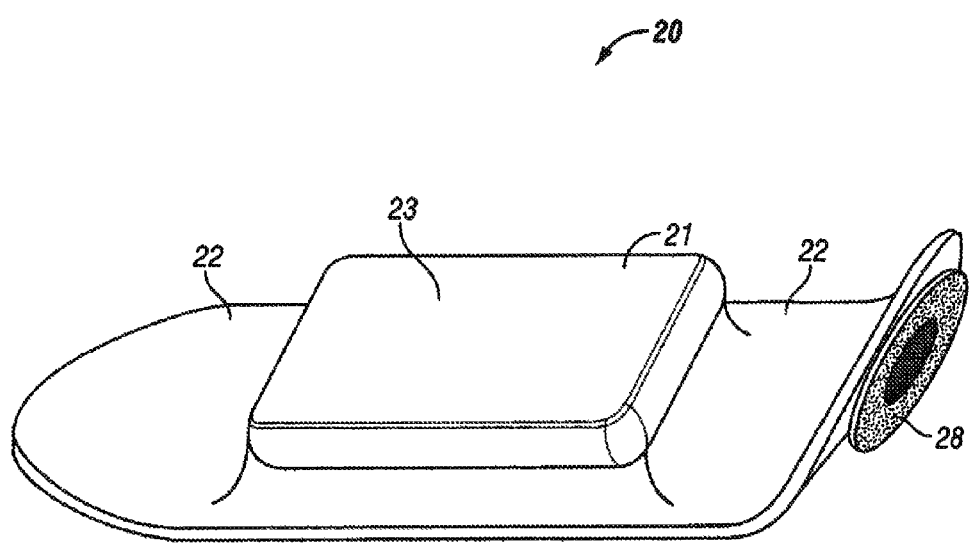
FIG. 2A is a perspective view of the vitals sign monitor patch shown in FIG. 1 according to certain aspects of the present disclosure.

FIG. 2A is a perspective view of the vital-signs monitor patch 20 shown in FIG. 1 according to certain aspects of the present disclosure. In the illustrated embodiment, the monitor patch 20 includes component carrier 23 comprising a central segment 21 and side segments 22 on opposing sides of the central segment 21. In certain embodiments, the central segment 21 is substantially rigid and includes a circuit assembly (24, FIG. 2B) having electronic components and battery mounted to a rigid printed circuit board (PCB). The side segments 22 are flexible and include a flexible conductive circuit (26, FIG. 2B) that connect the circuit assembly 24 to electrodes 28 disposed at each end of the monitor patch 20, with side segment 22 on the right shown as being bent upwards for purposes of illustration to make one of the electrodes 28 visible in this view.

Figure 2B:
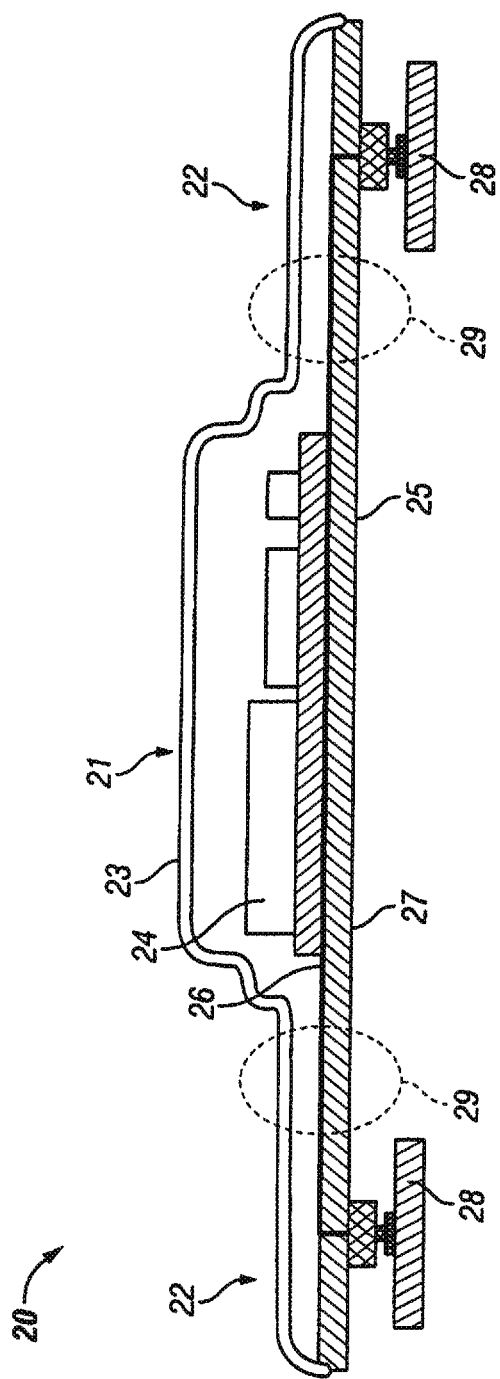
FIG. 2B is a cross-sectional view of the vital signs patch shown in FIGS. 1 and 2A according to certain aspects of the present disclosure.

FIG. 2B is a cross-sectional view of the vital-signs patch 20 shown in FIGS. 1 and 2A according to certain aspects of the present disclosure. The circuit assembly 24 and flexible conductive circuit 26 described above can be seen herein. The flexible conductive circuit 26 operably connects the circuit assembly 24 to the electrodes 28. Top and bottom layers 23 and 27 form a housing 25 that encapsulate circuit assembly 28 to provide a water and particulate barrier as well as mechanical protection. There are sealing areas on layers 23 and 27 that encircles circuit assembly 28 and is visible in the cross-section view of FIG. 2B as areas 29. Layers 23 and 27 are sealed to each other in this area to form a substantially hermetic seal. Within the context of certain aspects of the present disclosure, the term 'hermetic' implies that the rate of transmission of moisture through the seal is substantially the same as through the material of the layers that are sealed to each other, and further implies that the size of particulates that can pass through the seal are below the size that can have a significant effect on circuit assembly 24. Flexible conductive circuit 26 passes through portions of sealing areas 29 and the seal between layers 23 and 27 is maintained by sealing of layers 23 and 27 to flexible circuit assembly 28. The layers 23 and 27 are thin and flexible, as is the flexible conductive circuit 26, allowing the side segment 22 of the monitor patch 20 between the electrodes 28 and the circuit assembly 24 to bend as shown in FIG. 2A.

Figure 2C:
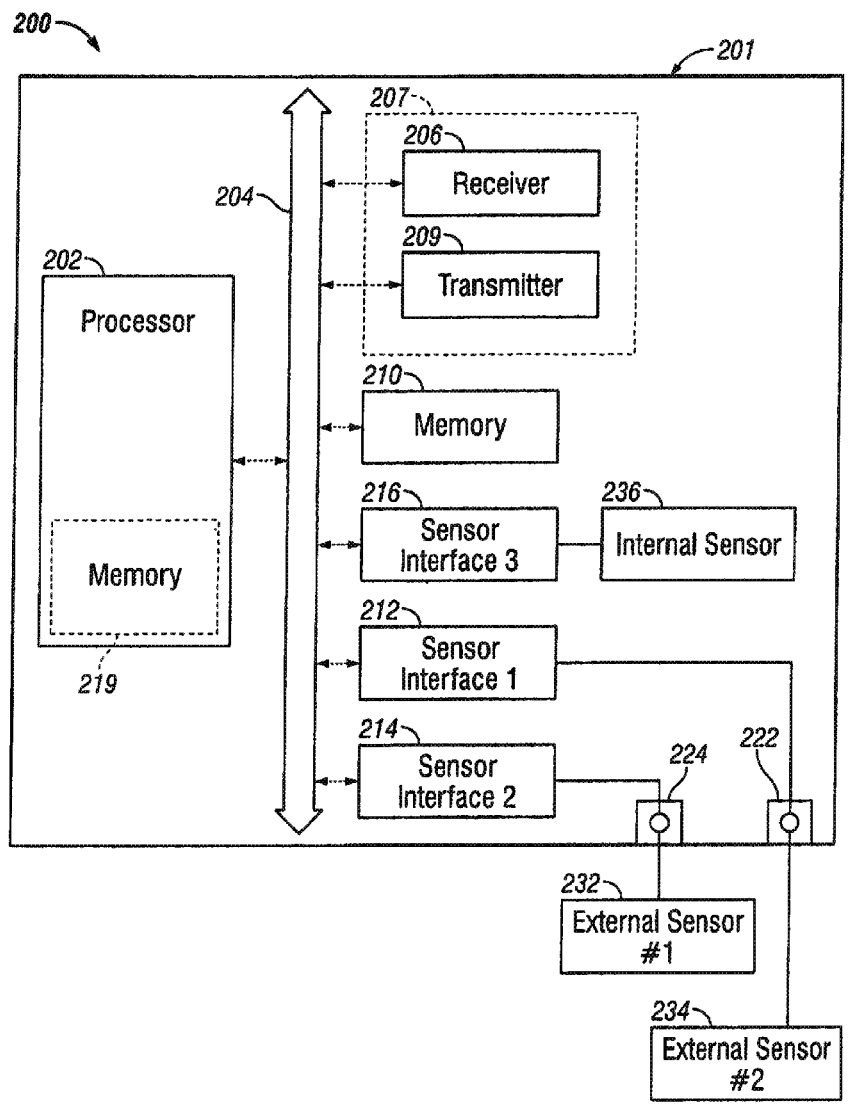
FIG. 2C is a functional block diagram illustrating exemplary electronic and sensor components of the monitor patch of FIG. 1 according to certain aspects of the present disclosure.

FIG. 2C is a functional block diagram 200 illustrating exemplary electronic and sensor components of the monitor patch 20 of FIG. 1 according to certain aspects of the present disclosure. The block diagram 200 shows a processing and sensor interface module 201 and external sensors 232, 234 connected to the module 201. In the illustrated example, the module 201 includes a processor 202, a wireless transceiver 207 having a receiver 206 and a transmitter 209, a memory 210, a first sensor interface 212, a second sensor interface 214, a third sensor interface 216, and an internal sensor 236 connected to the third sensor interface 216. The first and second sensor interfaces 212 and 214 are connected to the first and second external sensors 232, 234 via first and second connection ports 222, 224, respectively. In certain embodiments, some or all of the aforementioned components of the module 201 and other components are mounted on a PCB.

Each of the sensor interfaces 212, 214, 216 can include one or more electronic components that are configured to generate an excitation signal or provide DC power for the sensor that the interface is connected to and/or to condition and digitize a sensor signal from the sensor. For example, the sensor interface can include a signal generator for generating an excitation signal or a voltage regulator for providing DC power to the sensor. The sensor interface can further include an amplifier for amplifying a sensor signal from the sensor and an analog-to-digital converter for digitizing the amplified sensor signal. The sensor interface can further include a filter (e.g., a low-pass or bandpass filter) for filtering out spurious noises (e.g., a 60 Hz noise pickup).

The processor 202 is configured to send and receive data (e.g., digitized signal or control data) to and from the sensor interfaces 212, 214, 216 via a bus 204, which can be one or more wire traces on the PCB. Although a bus communication topology is used in this embodiment, some or all communication between discrete components can also be implemented as direct links without departing from the scope of the present disclosure. For example, the processor 202 may send data representative of an excitation signal to the sensor excitation signal generator inside the sensor interface and receive data representative of the sensor signal from the sensor interface, over either a bus or direct data links between processor 202 and each of sensor interface 212, 214, and 216.

The processor 202 is also capable of communication with the receiver 206 and the transmitter 209 of the wireless transceiver 207 via the bus 204. For example, the processor 202 using the transmitter and receiver 209, 206 can transmit and receive data to and from the bridge 40. In certain embodiments, the transmitter 209 includes one or more of an RF signal generator (e.g., an oscillator), a modulator (a mixer), and a transmitting antenna; and the receiver 206 includes a demodulator (a mixer) and a receiving antenna which may or may not be the same as the transmitting antenna. In some embodiments, the transmitter 209 may include a digital-to-analog converter configured to receive data from the processor 202 and to generate a base signal; and/or the receiver 206 may include an analog-to-digital converter configured to digitize a demodulated base signal and output a stream of digitized data to the processor 202.

The processor 202 may include a general-purpose processor or a specific-purpose processor for executing instructions and may further include a memory 219, such as a volatile or non-volatile memory, for storing data and/or instructions for software programs. The instructions, which may be stored in a memory 219 and/or 210, may be executed by the processor 202 to control and manage the wireless transceiver 207, the sensor interfaces 212, 214, 216, as well as provide other communication and processing functions.

The processor 202 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information, such as program instructions, data representative of sensor readings, preset alarm conditions, threshold limits, may be stored in a computer or processor readable medium such as a memory internal to the processor 202 (e.g., the memory 219) or a memory external to the processor 202 (e.g., the memory 210), such as a Random Access Memory (RAM), a flash memory, a Read Only Memory (ROM), a Programmable Read-Only Memory (PROM), an Erasable PROM (EPROM), registers, a hard disk, a removable disk, or any other suitable storage device.

In certain embodiments, the internal sensor 236 can be one or more sensors configured to measure certain properties of the processing and sensor interface module 201, such as a board temperature sensor thermally coupled to a PCB. In other embodiments, the internal sensor 236 can be one or more sensors configured to measure certain properties of the patient 10, such as a motion sensor (e.g., an accelerometer) for measuring the patient's motion.

The external sensors 232, 234 can include sensors and sensing arrangements that are configured to produce a signal representative of one or more vital signs of the patient to which the monitor patch 20 is attached. For example, the first external sensor 232 can be a set of sensing electrodes that are affixed to an exterior surface of the monitor patch 20 and configured to be in contact with the patient for measuring the patient's respiratory rate, and the second external sensor 234 can include a temperature sensing element (e.g., a thermocouple or a thermistor) affixed, either directly or via an interposing layer, to skin of the patient 10 for measuring the patient's body temperature. In other embodiments, one or more of the external sensors 232, 234 or one or more additional external sensors can measure other vital signs of the patient, such as blood pressure and pulse rate.

Figure 3A:
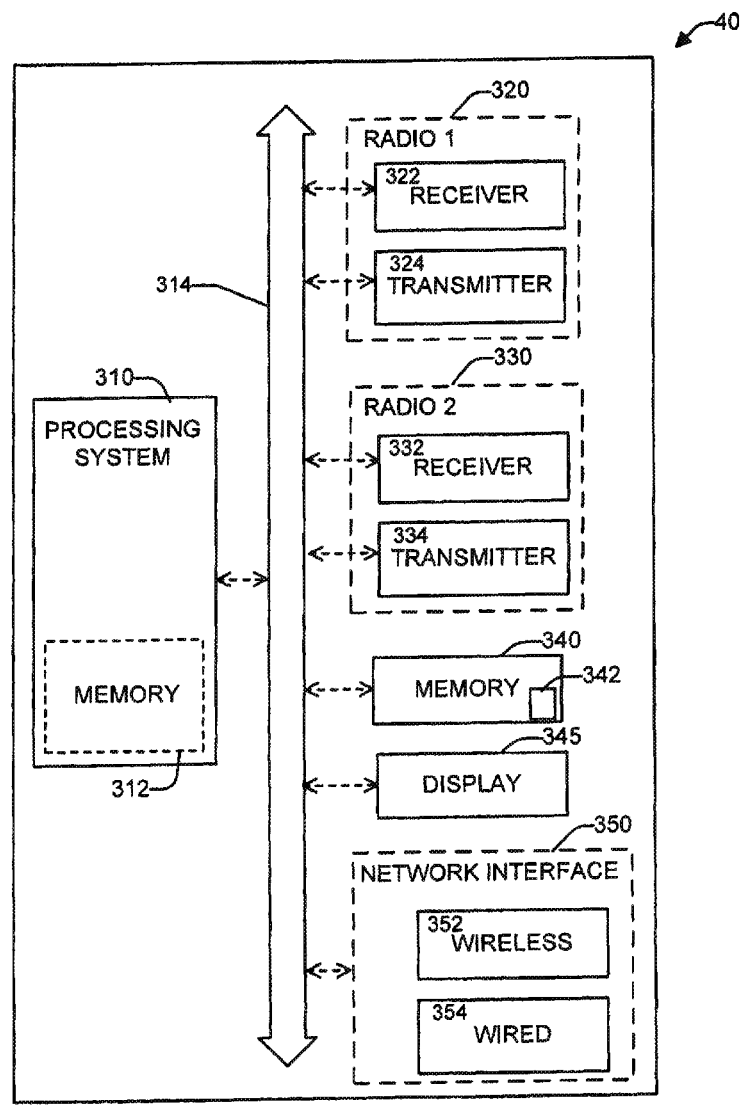
FIG. 3A is a functional schematic diagram of an embodiment of the bridge according to certain aspects of the present disclosure.

FIG. 3A is a functional block diagram illustrating exemplary electronic components of bridge 40 of FIG. 1 according to one aspect of the subject disclosure. Bridge 40 includes a processor 310, radio 320 having a receiver 322 and a transmitter 324, radio 330 having a receiver 332 and a transmitter 334, memory 340, display 345, and network interface 350 having a wireless interface 352 and a wired interface 354. In some embodiments, some or all of the aforementioned components of module 300 may be integrated into single devices or mounted on PCBs.

Processor 310 is configured to send data to and receive data from receiver 322 and transmitter 324 of radio 320, receiver 332 and transmitter 334 of radio 330 and wireless interface 352 and wired interface 354 of network interface 350 via bus 314. In certain embodiments, transmitters 324 and 334 may include a radio frequency signal generator (oscillator), a modulator, and a transmitting antenna, and the receivers 322 and 332 may include a demodulator and antenna which may or may not be the same as the transmitting antenna of the radio. In some embodiments, transmitters 324 and 334 may include a digital-to-analog converter configured to convert data received from processor 310 and to generate a base signal, while receivers 322 and 332 may include analog-to-digital converters configured to convert a demodulated base signal and sent a digitized data stream to processor 310.

Processor 310 may include a general-purpose processor or a specific-purpose processor for executing instructions and may further include a memory 312, such as a volatile or non-volatile memory, for storing data and/or instructions for software programs. The instructions, which may be stored in memories 312 or 340, may be executed by the processor 310 to control and manage the transceivers 320, 330, and 350 as well as provide other communication and processing functions.

Processor 310 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as data representative of sensor readings may be stored in memory 312 internal to processor 310 or in memory 340 external to processor 310 which may be a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD), or any other suitable storage device.

Memory 312 or 340 can also store a list or a database of established communication links and their corresponding characteristics (e.g., signal levels) between the bridge 40 and its related monitor patches 20. In the illustrated example of FIG. 3A, the memory 340 external to the processor 310 includes such a database 342; alternatively, the memory 312 internal to the processor 310 may include such a database.

Figure 3B:
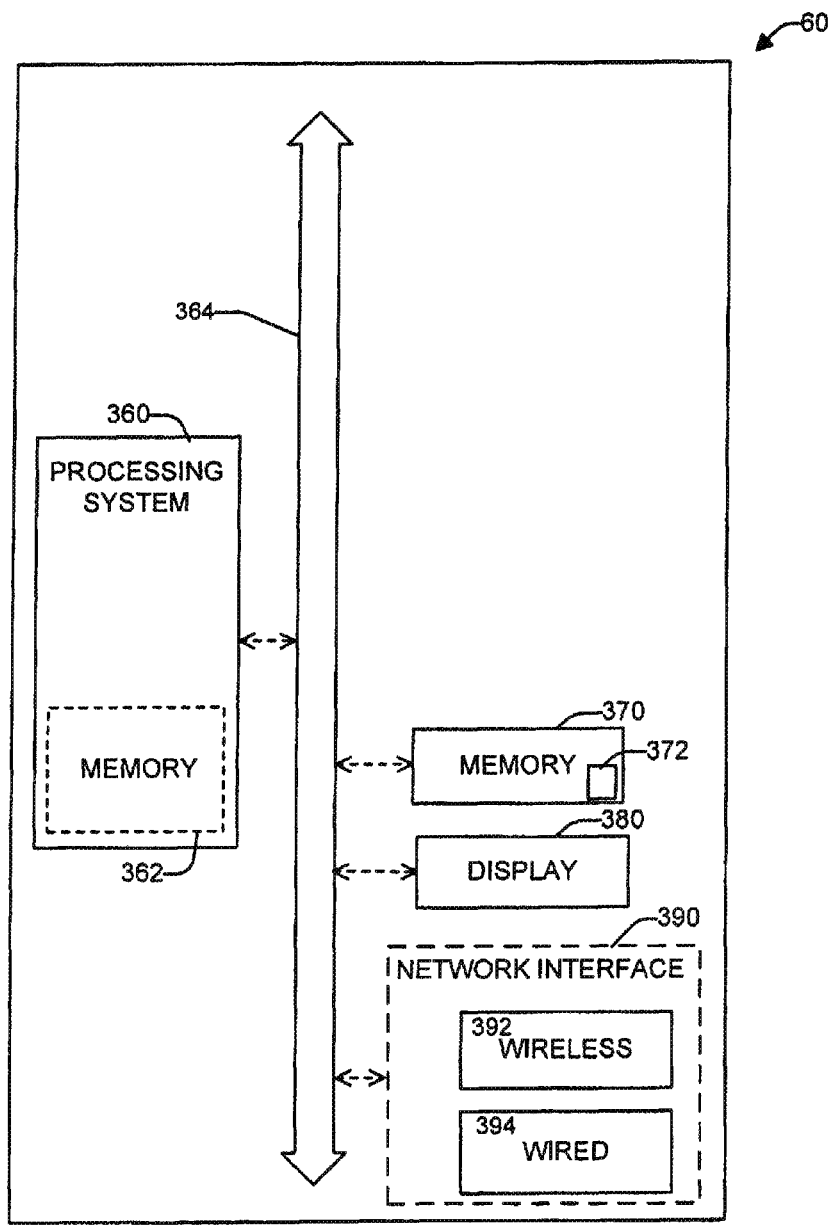
FIG. 3B is a functional schematic diagram of an embodiment of the surveillance server according to certain aspects of the present disclosure.

FIG. 3B is a functional block diagram illustrating exemplary electronic components of server 60 of FIG. 1 according to one aspect of the subject disclosure. Server 60 includes a processor 360, memory 370, display 380, and network interface 390 having a wireless interface 392 and a wired interface 394. Processor 360 may include a general-purpose processor or a specific-purpose processor for executing instructions and may further include a memory 362, such as a volatile or non-volatile memory, for storing data and/or instructions for software programs. The instructions, which may be stored in memories 362 or 370, may be executed by the processor 360 to control and manage the wireless and wired network interfaces 392, 394 as well as provide other communication and processing functions.

Processor 360 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as data representative of sensor readings may be stored in memory 362 internal to processor 360 or in memory 370 external to processor 360 which may be a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD), or any other suitable storage device.

Memory 362 or 370 can also store a database of communication links and their corresponding characteristics (e.g., signal levels) between monitor patches 20 and bridges 40. In the illustrated example of FIG. 3B, the memory 370 external to the processor 360 includes such a database 372; alternatively, the memory 362 internal to the processor 360 may include such a database.

Figure 4A:
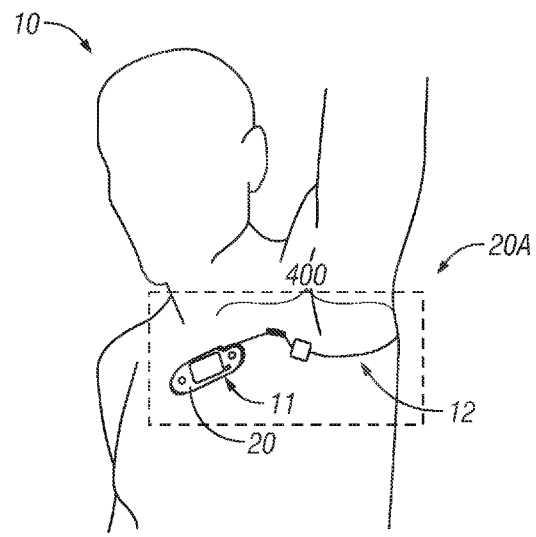
FIG. 4A is a diagram depicting a patient wearing a temperature monitoring system comprising a monitor patch and a temperature probe and configured to measure body temperature of the patient according to certain aspects of the present disclosure.

As indicated above with respect to FIG. 2C, certain embodiments of the monitor patch 20 are configured to operate with external sensors that are in turn configured to produce a signal representative of one or more vital signs of the patient to whom the monitor patch 20 is attached. For example, the second external sensor 234 can be a temperature probe that includes a temperature sensing element (e.g., a thermocouple or thermistor) affixed, either directly or via an interposing layer, to skin of the patient 10 for measuring the patient's body temperature. FIG. 4A is a diagram depicting a patient 10 wearing a temperature monitoring system 20A comprising a monitor patch 20 and a temperature probe 400 that is configured to measure body temperature of the patient 10. In the illustrated example, the temperature probe 400 is configured for axillary temperature sensing of the patient 10 to whom the monitor patch 20 is attached. The monitor patch 20 is attached to the chest 11 of the patient 10, with a sensing portion of the temperature probe 400 retained in the axilla 12 of the patient 10 during body temperature monitoring.

Figure 4B:
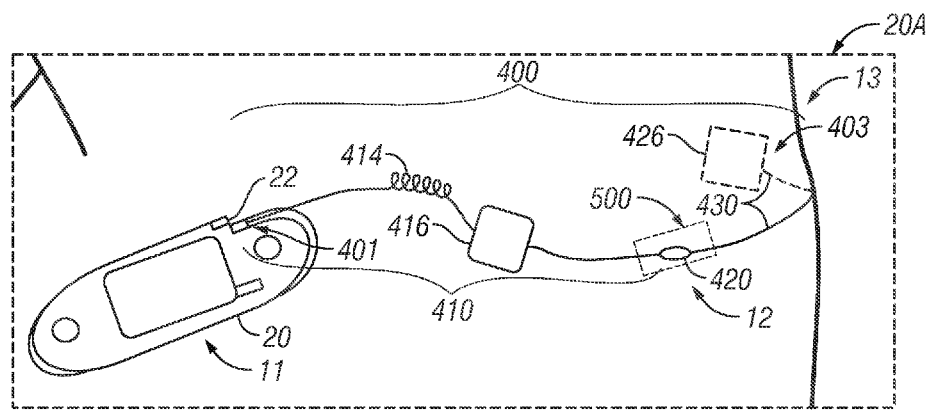
FIG. 4B is a diagram providing an enlarged view of the temperature monitoring system depicted in FIG. 4A according to certain aspects of the present disclosure.

FIG. 4B is a diagram providing an enlarged view of the monitoring system 20A depicted in FIG. 4A according to certain aspects of the present disclosure. As indicated above, the monitor patch 20 is attached to the chest 11 of the patient 10 via, e.g., an adhesive backing (not shown). The temperature probe 400 has a proximal end 401 and a distal end 403 and includes a wiring portion 410, a body connection portion 430, and a sensing portion 420 disposed between the wiring and body connection portions 410, 430. The proximal end 401 of the temperature probe 400 is connected to the monitor patch 20 at its connection port 22. In certain embodiments, the proximal end 401 of the temperature probe 400 is removably attached (e.g., plugged) to the monitor patch 20. In other embodiments, the proximal end 401 is fixedly attached (e.g., epoxied or fused) to the monitor patch 20.

The sensing portion 420 of the temperature probe 400 is configured for placement within the axilla 12 of the patient 10 and includes a temperature sensing element (e.g., 234A-D of FIGS. 5A-D and 234E-F of FIGS. 6A-B). The wiring portion 410 of the temperature probe 400 includes one or more electrical conductors (512, 514 of FIGS. 5A-D and FIGS. 6A-B) for carrying a signal responsive to a change in body temperature of the patient 10 between the temperature sensing element 234 and the monitor patch 20. In the illustrated example, the wiring portion 410 includes a flexible cable comprising a tubing and electrical conductors (e.g., a pair of twisted copper wires) placed within the tubing. The wiring portion 410 includes a coiled section 414 acting as a spring to take up any slack in the cable so as to accommodate patients of different sizes. In the illustrated example, the monitoring system 20A further includes an adhesive element 416 (e.g., a tape) coupled to the cable and configured to attach the wiring portion 410 of the cable to the patient's body, e.g., at a point between the chest 11 and the armpit 12 of the patient.

The body connection portion 430 has one end connected to the sensing portion 420 and is configured to be attached to another body portion of the patient 10 such that the sensing portion 420 of the temperature probe 400 can be retained within the axilla 12 of the patient 10. In the illustrated example, such attachment is achieved via an adhesive element 426 (e.g., a tape) coupled to the distal end of the body connection portion 430. The coupled adhesive element 426 is then attached to a second body portion 13 (e.g., the back of the patient's arm) of the patient 10.

A multitude of modifications and additions to the illustrated embodiment of FIG. 4B are possible without departing from the scope of the disclosure. For example, the body connection portion 430 of the temperature probe 400 can include one or more coiled sections acting as a spring similar to the coiled section 414 of the wiring portion 410. The adhesive element 416 may be coupled to the body connection portion 430 at a point different than the distal end of the body connection portion 430. In certain embodiments, entirely different means of attaching the body connection portion 430 to the patient's body may be used. For example, the body connection portion 430 may itself be in the form of an adhesive tape that can stick to the body of the patient 10 or may include an elastic loop (e.g., a rubber band) to be placed around the patient's arm.

While the temperature probe 400 in the illustrated embodiments of FIGS. 4A-B is shown to be operatively coupled to a vital-sign monitor patch worn by the patient 10, the temperature probe 400 may be alternatively operatively coupled to other types of monitoring devices such as a stationary monitoring unit located near the patient's hospital bed. Such a stationary monitoring unit can take readings of the patient's body temperature based on a signal from the temperature probe 400 and send the temperature readings to a surveillance server via a wired or wireless connection and make other decisions such as providing an indication of an alarm condition (e.g., a high body temperature condition or a loss of thermal contact between the temperature probe and the patient).

An important concept in the vital-sign monitoring system of the present disclosure is "measurement interval," or "sampling rate," which is an inverse of the measurement interval. In certain embodiments, the monitor patch generates data samples of a vital sign or vital signs of a patient at a predetermined measurement interval or sampling rate and transmits the data samples to a surveillance server, either directly or via a bridge. In some embodiments, the default measurement interval is 10 minutes, providing, for example, about 5 days of operation for a disposable monitor patch. Measurement intervals can be set at the hospital or care unit level and can be set to a value in a range of between about 2 and 30 minutes. Because vital-sign measurements and transmissions account for a significant portion of power consumption for a monitor patch, a measurement-interval setting directly impacts the life expectancy of the monitor patch.

In certain embodiments, the monitoring system can dynamically adjust the measurement interval (hence the sampling rate) depending on values of the vital sign or vital signs of interest. For example, under normal patient conditions, the monitor patch generates data samples at a first (normal) sampling rate. When an alert condition is detected (e.g., a vital-sign value reaching and staying above a threshold limit), the monitor patch can automatically change from the first (normal) sampling rate (e.g., every 10 minutes) to a second (alert) sampling rate (e.g., every 2 minutes). The monitor patch can also revert to the first (normal) sampling rate when the vital-sign value returns to a value below the threshold limit.

Figure 5:
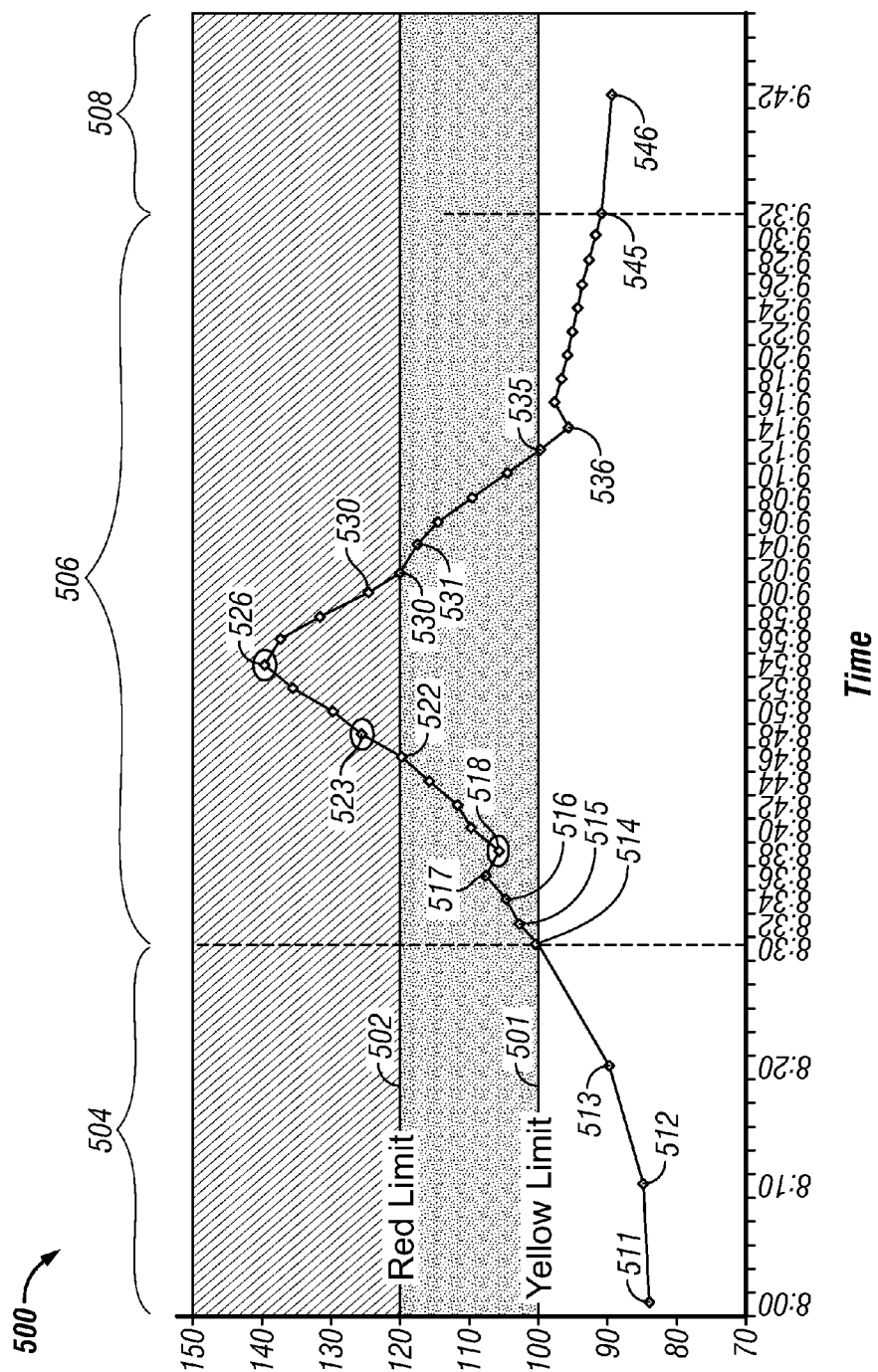
FIG. 5 depicts a graph representing a series of data samples corresponding to a vital sign of a patient generated by a monitor patch according to certain aspects of the present disclosure.

FIG. 5 depicts a graph 500 representing a series of data samples (solid dots) corresponding to vital-sign values of a patient generated by a monitor patch (e.g., 20 of FIGS. 4A and 4B) according to certain aspects of the present disclosure. The vital-sign values can represent, for example, body temperature or heart rate of the patient. The graph 500 shows two threshold limits: a first threshold limit 501 (the "yellow limit") and a second threshold limit 502 (the "red limit"). The graph 500 is divided into three regions: a first region 504 corresponding to the monitor patch 20 operating in a normal mode, a second region 506 corresponding to the monitor patch 20 operating in an alert mode, and a third region 508 corresponding to the monitor patch 20 reverting to its normal mode of operation.

Figure 6:
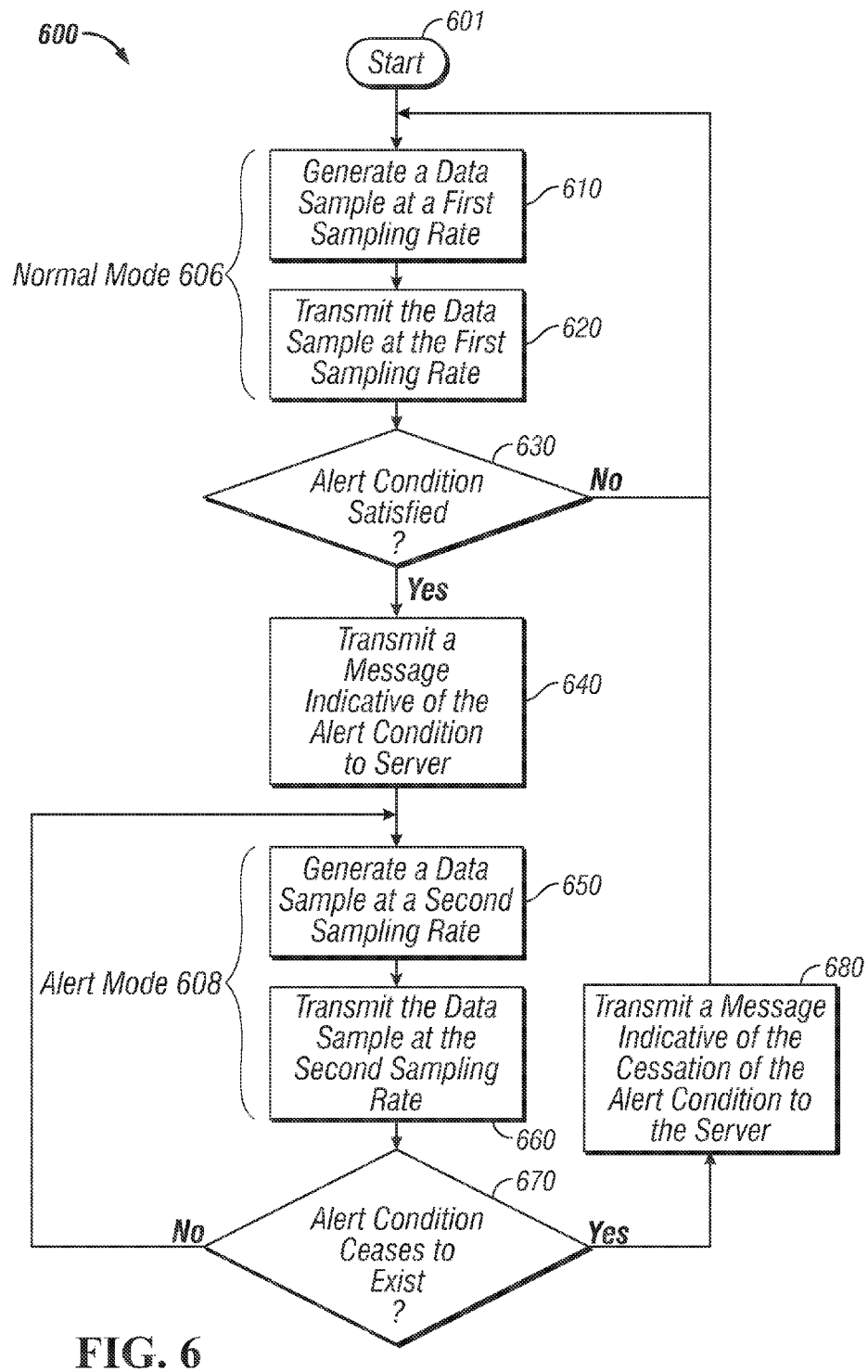
FIG. 6 is a flowchart illustrating an exemplary vital-sign monitoring process from the perspective of a vital-sign monitor patch according to certain aspects of the present disclosure.

FIG. 6 is a flowchart illustrating an exemplary vital-sign monitoring process 600 from the perspective of a vital-sign monitor patch according to certain aspects of the present disclosure. For the purposes of illustration only, without any intent to limit the scope of the present disclosure in any way, the process 600 will be described with reference to the graph 500 of FIG. 5. The process 600 begins at start state 601 and proceeds to operation 610 in which the monitor patch 20 generates a data sample of a vital sign of a patient at a first (normal) sampling rate (e.g., after a first measurement interval from a previous data sample). At this stage, the monitor patch 20 is assumed to be in a normal mode of operation 606 corresponding to, e.g., the first region 504 of FIG. 5. In the illustrated example, the first sampling rate is one data sample per every 8 minutes corresponding to a first (normal) measurement interval of 8 minutes. In certain embodiments, an analog-to-digital converter in a sensor interface (e.g., 212, 214 of FIG. 2C) of the monitor patch 20 converts a sensor signal indicative of a vital sign (e.g., a patient's respiration, heart beat, or body temperature) into digital representations of the sensor signal, a processor (e.g., 202 of FIG. 1) in the monitor patch 20 reads the data samples 511-514, processes them and generates data samples (e.g., vital-sign values) of the vital sign based on, e.g., an equation or a lookup table stored in a memory (e.g., 219, 210 of FIG. 2C).

In certain embodiments, the monitor patch 20 captures multiple readings of the sensor signal during the normal measurement interval (e.g., 8 minutes) before generating a data sample. For example, the monitor patch 20 can read the sensor signal enough times for a signal processing algorithm coded into the patch firmware to identify certain relevant features of the waveform and to calculate the values. In one exemplary embodiment, the sensor signal is read at 250 samples per second, and the processor converts (e.g., calculates and averages) the multiple readings (e.g., 2000 readings) into one data sample at the end of the normal measurement interval.

The process 600 proceeds to operation 620 in which each of the data samples 511-514 thus generated is transmitted to a surveillance server 60 either directly or via a bridge. That is, the monitor patch transmits the data samples to either a bridge (e.g., 40 FIG. 1), which then transmits the data sample to the server 60 either directly or via a bridge 40. Such data samples representing vital-sign values of a patient may be displayed on a display terminal or logged in a database. The monitor patch is still considered to be in the normal mode of operation 606 at this stage.

The process 600 proceeds to decision state 630 in which it is determined whether the generated data sample satisfies an alert condition. In the illustrated example of FIG. 5, the alert condition includes one data sample being at or above the first threshold limit 501. In the illustrated example of FIG. 5, data sample 514 has reached the first threshold limit 514, thereby satisfying the alert condition. In other embodiments, the alert condition may include 2 or more consecutive samples being at or above the first threshold limit 501.

If it is determined at the decision state 630 that the alert condition is not satisfied (No), the process 600 loops back to the operation 610 where another data sample is generated. On the other hand, if it is determined at the decision state 630 that the alert condition is satisfied (Yes) as a result of, for example, one or more data samples being at or above the first threshold limit, the process 600 proceeds to operation 640 in which a message indicative of the alert condition is transmitted to the surveillance server 60 either directly or via a bridge 40.

The process 600 then proceeds to operation 650 in which a data sample is generated at a second (alert) sampling rate (i.e., after a second measurement interval from a previous data sample), where the second sampling rate is higher than the first sampling rate. In the illustrated example of FIG. 5, the second sampling rate is one data sample per every 2 minutes corresponding to a second (alert) measurement interval of 2 minutes. At this stage, the monitor patch 20 is considered to be in an alert mode of operation 608 corresponding to, e.g., the second region 506 of FIG. 5. In certain embodiments, the monitor patch 20 captures multiple readings of the sensor signal during the second measurement interval (e.g., 2 minutes) and converts the multiple readings into one data sample at the end of the measurement interval. The process 600 proceeds to operation 660 in which each of data samples 515-545 thus generated is transmitted to the surveillance server 60 either directly or via a bridge 40 at the second sampling rate.

The process 600 then proceeds to decision state 670 in which it is determined whether the alert condition that caused the monitor patch to enter the alert mode 608 has ceased to exist. In certain embodiments, the alert condition is considered to have ceased to exist when the most recent data samples of the vital sign are less than the first threshold limit 501 consecutively for a predetermined number (e.g., 1-20) of times. For example, in the illustrated example of FIG. 5, data samples 536-545 have fallen below the first threshold limit 501 and remain consecutively so for 10 times. Assuming that the predetermined number is 10, the monitor patch determines that the alert condition has ceased to exist.

If it is determined at the decision state 670 that the alert condition still exists (No), the process 600 proceeds to the operation 650 where a next data sample is generated and then to the operation 660 where the next data sample is transmitted to the surveillance server. On the other hand, if it is determined at the decision state 670 that the alert condition has ceased to exist (Yes), the process 600 exits the alert mode 608 and proceeds to operation 680 in which a message indicative of the cessation of the alert condition is transmitted to the surveillance server either directly or via a bridge and then back to the operation 610 in the normal mode 606 (corresponding to the third region 508 of FIG. 5), where data samples are again generated at the first sampling rate starting with data sample 546.

Figure 7:
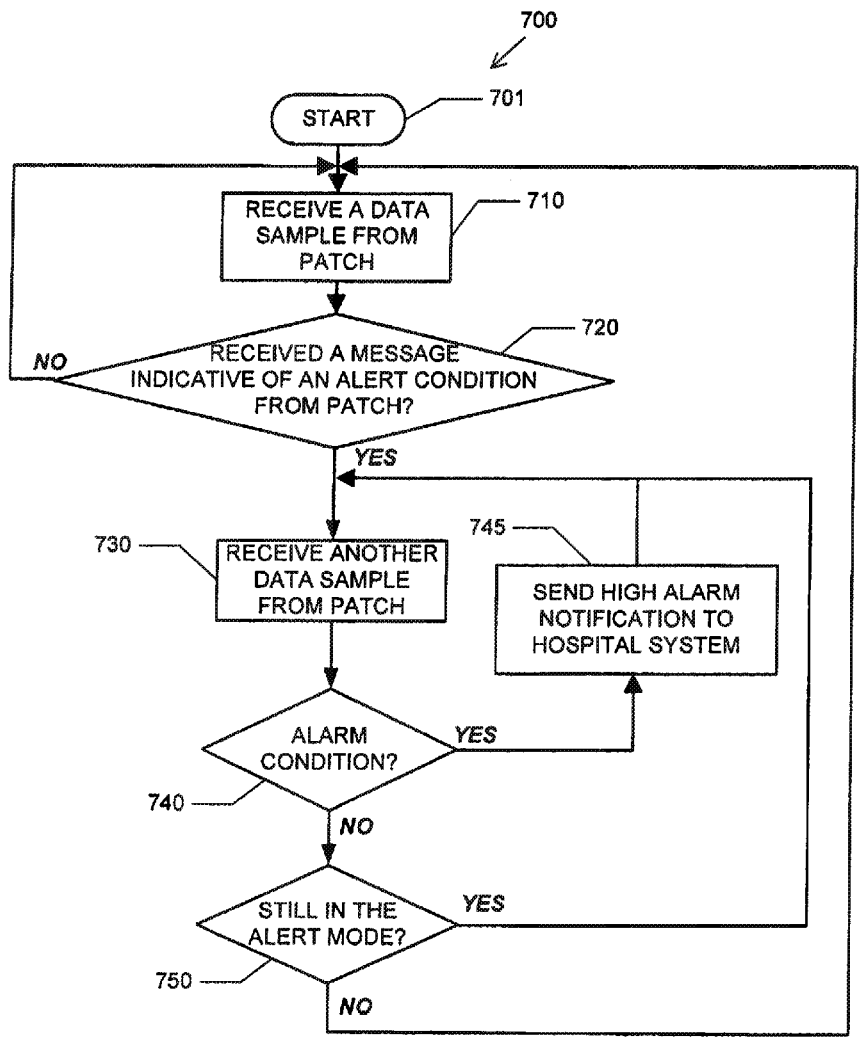
FIG. 7 is a flowchart illustrating an exemplary vital-sign monitoring process from the perspective of a surveillance server according to certain aspects of the present disclosure.

FIG. 7 is a flowchart illustrating an exemplary vital-sign monitoring process 700 from the perspective of a surveillance server (e.g., 60 of FIG. 1) according to certain aspects of the present disclosure. For the purposes of illustration only, without any intent to limit the scope of the present disclosure in any way, the process 700 will be described with references to the graph 500 of FIG. 5 and the process 600 of FIG. 6. The process 700 begins at start state 701 and proceeds to operation 710 in which a data sample from the vital-sign monitor patch 20 referenced above with respect to FIG. 6 is received. Without loss of generality, it is assumed that the data sample was sent while the monitor patch 20 was in the normal mode of operation 606. Therefore, at this point in the process, such data samples are received at the first (normal) sampling rate. The surveillance server 60 may, in some embodiments, send the data samples to a hospital system (e.g., 100 of FIG. 1) to be displayed on a display terminal or logged in a database.

The process 700 proceeds to decision state 710 in which it is determined whether the surveillance server has received a message indicative of the alert condition sent from the monitor patch 20 as discussed above with respect to the operation 640 of FIG. 6. If it is determined at the decision state 710 that such a message has not been received by the surveillance server (No), the process 700 loops back to the operation 710 where the surveillance server 60 waits for and receives another data sample from the monitor patch 20.

On the other hand, if it is determined at the decision state 720 that such a message has been received by the surveillance server 60 (Yes), the process 700 proceeds to operation 730 in which the surveillance server 60 waits for and receives a next data sample from the monitor patch 20 at the second (alert) sampling rate and then to decision state 740 in which it is determined whether one or more most recently received data samples including the present data sample satisfy an alarm condition. In certain embodiments, the alarm condition includes the set of data samples having been at or above a threshold limit (e.g., the first threshold limit 501 of FIG. 5) and rising consecutively for a predetermined number of times. For example, a processor in the surveillance server 60 can perform such an alarm condition determination.

If it is determined at the decision state 740 that the alarm condition has been satisfied, the process 700 proceeds to operation 745 in which an alarm notification is sent to the hospital system (e.g., 100 of FIG. 1). In the illustrated example of FIG. 5, a first alarm notification is sent to the hospital system upon receiving data sample 517, which corresponds to a fifth consecutively rising data sample after the vital sign has reached the first threshold limit 501. Subsequently, a second alarm notification is sent to the hospital system upon receiving data sample 523, which corresponds to a second consecutively rising data sample after the second (e.g., danger) threshold limit 502 has been reached. In certain embodiments, after an alarm notification is sent after reaching a threshold limit, a current data sample is compared to a previously notified data sample (data sample at which a previous alarm notification was sent), and a new alarm notification is sent if a difference between the current data sample and the previously notified data sample exceeds a certain threshold difference value. In the illustrated example, based on this algorithm, a third alarm notification is sent to the hospital system upon receiving data sample 526 because the difference between the data sample 526 and the previously notified data sample 523 has exceeded a threshold difference value (e.g., 12).

Therefore, in certain algorithmic embodiments of the present disclosure, an alarm notification is sent when a current data sample exceeds a threshold high limit (e.g., 501, 502) and satisfies one of the following "high" conditions:

1) The current data sample corresponds to $X^{th}$ consecutively rising data sample after initially crossing the threshold high limit.
2) A difference between the current data sample and a previously notified data sample has exceeded a certain threshold difference value.

The first high condition can server the purpose of providing an alarm notification indicative of a crossing of the threshold high limit (warning or danger). The second high condition cam serve the purpose of providing an alarm notification indicative of a progressively worsening condition (e.g., rapidly rising temperature).

The hospital system may use the received notification, for example, to cause a nurse or doctor responsible for the patient to either monitor the progress of the condition in case of the first and second alarm notifications or to take certain actions (e.g., administering of a fever-reducing medication) in case of the third alarm notification.

The above-described algorithmic embodiments related to sending of an alarm notification when the current data sample exceeds a threshold high limit (e.g., 501, 502). In other embodiments, an alarm notification can be sent when the current data sample is below a low threshold limit (e.g., a first or second threshold limit) and satisfied one or more additional low conditions, examples of which include:

1) The current data sample corresponds to $Y^{th}$ consecutively falling data sample after initially crossing the low threshold limit.
2) A difference between a previously notified data sample and the current data sample has exceeded a certain threshold difference value.

Similar to the high conditions described above, the first low condition can serve the purpose of providing an alarm notification indicative of crossing of a threshold limit (warning or danger). The second low condition can serve the purpose of providing an alarm notification indicative of a progressively worsening condition (e.g., rapidly falling heart rate).

While the alarm notification algorithms have been described with respect to a particular vital-sign measurand, either an increase or decrease of any or all of multiple vital-signs that the monitor patch 20 is configured to monitor can cause an alarm notification to be sent. For example, assuming that a monitor patch 20 is configured to monitor three vital signs (e.g., heart rate, respiratory rate, and temperature), there can be 12 threshold limits (two high limits and two low limits for each of the three vital signs).

On the other hand, if it is determined at the decision state 740 that the one or more recently received data samples do not satisfy an alarm condition (No), the process 700 proceeds to decision state 750 in which it is determined whether the monitor patch 20 is still in the alert mode. In certain embodiments, this determination involves checking to determine if a message indicative of the cessation of the alert condition such as the one discussed above with respect to the operation 680 of FIG. 6 was received from the monitor patch 20. In other embodiments, this determination involves the surveillance server 60 applying the same criteria as the monitor patch 20 to the received data samples to determine whether the alert condition has ceased to exist. For example, the surveillance server can independently determine that the received data samples 536-545 have been below the first threshold limit 501 for 10 consecutive times.

If it is determined at the decision state 750 that the monitor patch has ceased to be in the alert mode (No), the process 700 loops back to the combination of operation 710 and decision state 720 where the surveillance server 60 receives more data samples at the first (normal) sampling rate and waits for a message indicative of another alert condition. On the other hand, if it is determined at the decision state 750 that the monitor patch 20 is still in the alert condition (Yes), the process 700 loops back to the operation 730 where the surveillance server 60 receives another data sample from the monitor patch 20 and then to the decision state 740 where the surveillance server 60 determines whether the alarm condition has been satisfied.

The processes 600 and 700 described above are for illustration only, and a multitude of additions, deletions, and modifications thereto are possible without departing from the scope of the present disclosure. For example, in certain alternative embodiments, a separate message indicative of the alert condition is not sent to the surveillance server as in the operation 640 of FIG. 6. Instead, the alert condition is indicated in the transmission of the data sample in the alert mode 608 at the operation 660. Similarly, a separate message indicative of the cessation of the alert condition may not be sent to the surveillance server as in the operation 680 of FIG. 6. Instead, the surveillance server can determine the cessation either from applying the criteria of the decision state 670 to the received data samples as discussed above or from an indication of the cessation included in the transmission of the received data samples. In some alternative embodiments, the surveillance server does not require a series of received samples to be consecutively rising as well as at or above a threshold limit for a predetermined number of times before sending the alert notification to the hospital system. As applied to the illustrated example of FIG. 5, in such an alternative embodiment, a fourth alarm notification would have been sent to the hospital system upon receiving data sample 530.

One skilled in the art would understand in view of the present disclosure that various systems and methods described above with respect to FIGS. 5-7 provide a number of important benefits to the vital-sign monitoring system of the present disclosure. For example, because a monitor patch 20 worn by a patient performs the highly power-consumptive data acquisition and transmission operations relatively infrequently while vital-sign values of the patient are normal (e.g., in the normal mode 606) and frequently only when the vital-sign values are abnormal (e.g., in the alert mode 608), the monitor patch 20 can exhibit significantly higher life-expectancy. Furthermore, from the perspective of a surveillance server 60, because data samples are received from the monitor patch 20 relatively infrequently while the patient's vital signs are normal, a significant reduction in the server's resources (e.g., processing time and memory space) can accrue.

In addition, the systems and methods provide for filtering out medically insignificant events that can otherwise trigger alarm notifications to the healthcare provider, thereby causing the provider to make unnecessary trips to the patient, for example. For instance, an electrical noise or movement of the patient may produce a short-lived spike (1 or 2 samples) in the measurements, but an influence of such a spike would be ignored by the alarm condition determination algorithm in the surveillance server 60. The aforementioned benefits can be obtained without sacrificing the response time of the monitoring system. For instance, in the illustrated example of FIG. 5, whenever vital sign values exceed a threshold limit (e.g., 501, 502), the vital-sign values can be displayed on a display terminal of the hospital system (e.g., 100 of FIG. 1) with a delay no longer than 2 minutes. Further, the time necessary for the values to be displayed on the display terminal is independent of the time necessary to transmit alarm notifications to the hospital system.

Certain aspects of the alert condition determination and the dynamic measurement interval adjustment described herein can be performed by the processor 202 (FIG. 2C) executing one or more sequences of one or more instructions using threshold limits and/or alert conditions contained in an internal machine-readable medium such as the internal memory 219 or the memory 210. For example, the processor 202 can determine that one or more vital-sign readings exceed the first threshold limit 501 and switch from a normal mode to an alert mode and change the sampling rate from a first rate to a second rate higher than the first rate. The processor 202 can also revert to the normal mode operation of the vital-sign readings return below the first threshold limit 501 and change the sampling rate from the second rate to the first rate.

The processor 202 may be a microprocessor, a microcontroller, a digital signal processor (DSP), or an application specific integrated circuit (ASIC) capable of executing computer instructions. Such instructions, threshold limits, and alert conditions may be read into the memory 219, 210 from another machine-readable medium, such as a CD, flash memory, or a wireless transmission. Execution of the sequences of instructions contained in the memory 219 causes the processor 202 to perform the process steps (e.g., of FIG. 6) described herein. One or more processors in a multi-processing arrangement may also be employed to execute the sequences of instructions contained in memory 219. In alternative embodiments, hard-wired circuitry may be used in place of or in combination with software instructions to implement various embodiments. Thus, embodiments are not limited to any specific combination of hardware circuitry and software.

Certain aspects of the alarm condition determination described herein can be performed by the processor 310 (FIG. 3) executing one or more sequences of one or more instructions using threshold limits and alarm conditions contained in an internal machine-readable medium such as the internal memory 312 or the memory 340. For example, the processor 310 can determine that one or more vital-sign readings exceed the first threshold limit 501 consecutively for a preset number of times and send a alarm notification. The processor 310 can also send the alarm notification more frequently if one or more vital-sign readings exceed the second threshold limit 502.

The processor 310 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Instructions, threshold limits, and alarm conditions may be read into the memory 312, 340 from another machine-readable medium, such as a CD, flash memory, or a wireless transmission. Execution of the sequences of instructions contained in the memory 312 causes the processor 310 to perform the process steps (e.g., of FIG. 7) described herein. One or more processors in a multi-processing arrangement may also be employed to execute the sequences of instructions contained in memory 312. In alternative embodiments, hard-wired circuitry may be used in place of or in combination with software instructions to implement various embodiments. Thus, embodiments are not limited to any specific combination of hardware circuitry and software.

The term "machine-readable medium" as used herein refers to any medium that participates in providing instructions to processor 202, 310 for execution or storing results of or parameters (e.g., variables or constants) for computations such as for the alert condition determination and the dynamic measurement interval adjustment by the processor 202 and the alarm condition determination by the processor 310. Such a medium may take many forms, including, but not limited to, non-volatile media, volatile media, and transmission media. Non-volatile media include, for example, optical or magnetic disks, such as data storage device. Volatile media include dynamic memory, such as the memory 210. Transmission media include coaxial cables, copper wire, and fiber optics, including the wires that comprise bus 204. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

The foregoing description is provided to enable any person skilled in the art to practice the various embodiments described herein. While the foregoing embodiments have been particularly described with reference to the various figures and embodiments, it should be understood that these are for illustration purposes only and should not be taken as limiting the scope of the claims.

The word "exemplary" is used herein to mean "serving as an example or illustration." Any aspect or design described herein as "exemplary" is not necessarily to be construed as preferred or advantageous over other aspects or designs.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A method of reducing false alarms associated with vital-sign monitoring, the method comprising the steps of:
    generating a plurality of data samples of a single vital sign of a patient during each of a series of normal measurement intervals in a normal mode of operation;
    converting the plurality of data samples generated during each of the series of normal measurement intervals to a single normal parameter value associated with the respective one of the series of normal measurement intervals;
    entering an alert mode of operation if the normal parameter value that is associated with the most recent of the series of normal measurement intervals is equal to or outside of a first threshold limit;
    generating a plurality of data samples of the single vital sign during one or more sequential alert measurement intervals while in the alert mode, an alert measurement interval being shorter than a normal measurement interval;
    converting the plurality of data samples generated during each of the one or more sequential alert measurement intervals to a single alert parameter value associated with the respective one of the one or more sequential alert measurement intervals; and
    providing a first alarm notification if a first alert parameter value is equal to or outside of a second threshold limit and a second alert parameter value is further outside the second threshold limit than the first alert parameter value, wherein the second alert parameter value is associated with an alert measurement interval that is immediately subsequent to the alert measurement interval associated with the first alert parameter value.

2. The method of claim 1, further comprising the step of:
    switching from the alert mode to the normal mode when a first predetermined number of most recent sequential alert parameter values are within the first threshold limit.

3. The method of claim 1, further comprising the step of:
    wirelessly sending the single normal parameter value to a surveillance server while in the normal mode.

4. The method of claim 3, further comprising the step of:
    wirelessly sending the single alert parameter value to a surveillance server while in the alert mode.

5. The method of claim 1, wherein the steps associated with generating a plurality of data samples, converting the plurality of data samples to the single normal or the single alert parameter value, entering an alert mode of operation, and providing an alarm notification are performed by a processor in a wireless vital-sign monitor patch.

6. The method of claim 1, further comprising the step of:
entering an alarm condition when a second predetermined number of most recent sequential alert parameters are rising consecutively.

7. The method of claim 6, further comprising the step of:
providing a second alarm notification when the alarm condition is entered.

8. A vital-sign monitor, comprising:
at least one sensor configured to generate a plurality of data samples of a single vital sign of a patient at a first sampling rate in a normal mode of operation;
a memory configured to store commands;
a processor configured to execute the commands stored in the memory, and upon execution of the commands, to cause the vital-sign monitor to:
convert the plurality of data samples generated at the first sampling rate to a single normal parameter value;
enter an alert mode if the single normal parameter value is equal to or outside of a first threshold limit;
generate with the at least one sensor a plurality of data samples of the single vital sign at a second sampling rate higher than the first sampling rate while in the alert mode; and
convert the plurality of data samples generated at the second sampling rate to a single alert parameter value; and
a wireless transceiver configured to provide an alarm notification to a surveillance server when a first alert parameter value is equal to or outside of a second threshold limit and a second alert parameter value immediately subsequent to the first alert parameter value is further outside the second threshold limit than the first alert parameter value, the wireless transceiver further configured to provide to the surveillance server the single normal parameter value while in the normal mode and the single alert parameter value while in the alert mode.

9. The vital-sign monitor of claim 8, wherein the vital-sign monitor is a wireless vital-sign monitor patch.

10. The vital-sign monitor of claim 8, wherein the at least one sensor comprises at least one of a body temperature sensor, a pulse rate sensor, a blood pressure sensor, and a respiratory rate sensor.

11. The vital-sign monitor of claim 8, wherein the processor is further configured to switch the at least one sensor from the alert mode to the normal mode when a predetermined number of the most recent alert parameter values are within the first threshold limit.

12. The vital-sign monitor of claim 8, wherein the wireless transceiver comprises a digital-to-analog converter configured to receive data from the processor and to generate a first base signal and an analog-to-digital converter configured to provide a digitized second base signal to the processor.

13. The vital-sign monitor of claim 8, wherein:
the vital-sign monitor is part of a vital-sign monitoring system, the system comprising;
a bridge configured to wirelessly receive the alert parameter values from the vital-sign monitor and provide the alert parameter values; and
the surveillance server, wherein the surveillance server is configured to communicate with the vital-sign monitor wirelessly through a bridge.

14. The vital-sign monitor of claim 13, wherein:
the bridge is further configured to receive and provide the single normal parameter value; and
the surveillance server is further configured to receive the single normal parameter value and send the single normal parameter value to the hospital system.

15. The vital-sign monitor of claim 8, wherein the processor is further configured to cause the wireless transceiver to transmit an alarm condition to the surveillance server when a second predetermined number of most recent sequential alert parameters are rising consecutively.

16. A method for providing an alarm in a vital-sign monitoring system, the method comprising the steps of:
causing a sensor in a vital sign monitor patch to measure a vital sign at a first frequency;
causing the sensor to measure the vital sign at a second frequency greater than the first frequency when the vital sign exceeds a first threshold while measuring the vital sign at the first frequency;
entering an alert mode of operation when the measured vital sign exceeds the first threshold while measuring the vital sign at the first frequency; and
causing a wireless transceiver to provide an alarm notification to a surveillance server when the measured vital sign initially exceeds a second threshold greater than the first threshold during a first time period while measuring the vital sign at the second frequency and the measured vital sign during a second time period of measuring the vital sign at the second frequency subsequent to the first time period exceeds the second threshold to a greater extent than the measured vital sign of the first time period.

17. The method of claim 16, further comprising selecting the second time period contiguous to the first time period.

18. The method of claim 16, further comprising selecting the first and second thresholds as upper limits and selecting the second threshold greater than the first threshold.

19. The method of claim 16, further comprising selecting the first and second thresholds as lower limits and selecting the second threshold lower than the first threshold.

* * * * *